United States Patent [19]

Dessau et al.

[11] Patent Number: 5,304,694
[45] Date of Patent: Apr. 19, 1994

[54] ISOBUTENE AND ISOAMYLENE PRODUCTION

[75] Inventors: Ralph M. Dessau, Edison; Quang N. Le, Cherry Hill, both of N.J.

[73] Assignee: Mobil Oil Corporation, Fairfax, Va.

[21] Appl. No.: 883,638

[22] Filed: May 15, 1992

Related U.S. Application Data

[60] Continuation of Ser. No. 418,377, Oct. 6, 1989, Pat. No. 5,192,728, which is a division of Ser. No. 211,198, Jun. 24, 1988, Pat. No. 4,990,710.

[51] Int. Cl.$^5$ .............................................. C07C 5/333
[52] U.S. Cl. .................................... 585/662; 585/660; 585/661
[58] Field of Search ................ 585/654, 660, 661, 662

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Van Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,663,493 | 5/1987 | Vora et al. | 585/665 |
| 4,830,729 | 5/1989 | Dessau et al. | 208/89 |
| 4,849,567 | 7/1989 | Dessau et al. | 585/379 |
| 4,851,599 | 7/1989 | Dessau | 585/407 |
| 4,868,145 | 9/1989 | Dessau et al. | 502/66 |
| 4,882,040 | 11/1989 | Dessau et al. | 208/138 |
| 4,886,926 | 12/1989 | Dessau et al. | 585/444 |
| 4,892,645 | 1/1990 | Dessau | 208/111 |
| 4,910,357 | 3/1990 | Dessau et al. | 585/322 |
| 4,935,566 | 6/1990 | Dessau et al. | 208/65 |
| 4,990,710 | 2/1991 | Dessau et al. | 585/277 |
| 5,037,529 | 8/1991 | Dessau et al. | 208/64 |
| 5,103,066 | 4/1991 | Dessau | 568/406 |
| 5,122,489 | 6/1992 | Dessau | 502/66 |
| 5,124,497 | 6/1992 | Dessau et al. | 585/419 |

FOREIGN PATENT DOCUMENTS

| | | |
|---|---|---|
| 18498 | 11/1980 | European Pat. Off. . |
| 2024790 | 5/1979 | United Kingdom . |
| 2033358A | 5/1980 | United Kingdom . |

*Primary Examiner*—Olik Chaudhuri
*Assistant Examiner*—C. Everhart
*Attorney, Agent, or Firm*—Alexander J. McKillop; Malcolm D. Keen; Marina V. Schneller

[57] ABSTRACT

Catalytic conversion of a $C_2$–$C_5$ alkane, e.g., isobutane and/or isopentane, to isoalkenes, e.g., isobutene and/or isopentene, respectively, is undertaken in the presence of an aromatic recycle stream which provides the heat of reaction for the conversion which is endothermic, in the absence of hydrogen.

32 Claims, No Drawings

ISOBUTENE AND ISOAMYLENE PRODUCTION

CROSS REFERENCE TO RELATED APPLICATION

This application is a continuation under 35 U.S.C. 120 of copending Ser. No. 418,377, filed Oct. 6, 1989 (now U.S. Pat. No. 5,192,728) which, in its entirety, is incorporated by reference herein, which in turn is a division of Ser. No. 211,198 filed Jun. 24, 1988 (now U.S. Pat. No. 4,990,710), which is relied upon and incorporated by reference herein.

FIELD OF THE INVENTION

This invention relates to catalytically converting $C_2$–$C_5$ alkanes to $C_2$–$C_5$ alkene(s). The catalytic conversion of $C_2$–$C_5$ alkane to the corresponding $C_2$–$C_5$ alkene is endothermic, in the absence of added hydrogen. The invention relates to heating the alkane in an aromatic recycle stream to an extent insufficient to substantially thermally degrade the aromatic recycle stream therein but sufficient to provide the heat input necessary to sustain the referred to conversion reaction, and, optionally, admixing such heated recycle with the fresh feed to such process.

The products of the specific processes of the invention, the production of isobutene and/or the isoamylenes (2-methylbutene-1 and 2-methylbutene-2) are particularly valuable in that each can be reacted with methanol to produce the methyl ether analog. The methyl ether analog of isobutene (t-butyl-methyl ether) and of the isopentene are valuable gasoline additives.

SUMMARY OF THE INVENTION

The process of the invention relates to the catalytic conversion of a $C_2$–$C_5$ alkane to the $C_2$–$C_5$ alkene in the presence of an aromatic recycle stream to produce the respective unsaturated analog.

The process comprises contacting a feed comprising isobutane and/or iso-pentane, with a non-acidic catalyst composition, in the presence of a heated aromatic recycle to produce the corresponding unsaturated analog together with $H_2$. The catalytic conversion exhibits high selectivity with respect to production of said unsaturated analog.

DETAILED DESCRIPTION OF THE INVENTION

The process comprises contacting a feed comprising a $C_2$–$C_5$ alkane with a non-acidic catalyst composition in the presence of a preheated aromatic recycle stream, to produce the corresponding unsaturated analog. The conversion of $C_2$–$C_5$ alkanes to $C_2$–$C_5$ olefins is endothermic.

The feed stream can be any feed stream containing a $C_2$–$C_5$ alkane, ethane, propane, butane, isobutane, pentane and/or isopentane; preferably the feed stream contains isobutane and/or isopentane, which are converted to isobutene and isopentene (the isoamylenes).

In accordance with the invention, catalytic conversion conditions include pressures varying from subatmospheric, to atmospheric to greater than atmospheric. Preferred pressures range from 0.1 atmospheres to atmospheric. However, pressures up to 500 psig can be employed. The catalytic conversion is conducted at elevated temperatures ranging from 400° C. to 700° C. and most preferably from 350° C. to 600° C. and most preferably at temperature ranging from 450°–600° C. The reactor inlet $H_2$/feed ratio is less than 5, preferably zero (0). However, in accordance with the invention, the process includes cofeeding hydrogen, in small amounts, e.g., of about 2–10% of the feed; such a hydrogen cofeed will improve catalyst stability, where the inlet temperature is above 590° C., although it will not enhance conversion or heat balance In particular, the conversion can be advantageously conducted at low hydrogen pressure; even at reactor inlet ratios of zero (0), there will be a hydrogen partial pressure in the reactor because hydrogen is a bi-product of the conversion. The weight hourly space velocity is 0.1 to 50, preferably 0.5 to 10.

The process of the conversion requires cofeeding to the catalytic conversion a preheated aromatic recycle stream to an extent insufficient to substantially thermally degrade the recycle stream therein but sufficient to provide additional heat input to sustain the referred to conversion reaction, and, optionally, admixing such heated recycle with the fresh feed to such process. Accordingly, the process of the invention requires providing a recycle stream which is heated to about the catalytic conversion temperature plus-or-minus 50° C. Practically, the recycle stream will be heated to 300° to 650° C. prior to introduction into the catalytic conversion zone. The recycle stream itself has an initial boiling point at least 40° C. above the end point of the feed containing the $C_2$–$C_5$ alkane. The recycle stream itself is preferably substantially constituted of aromatic components. Preferably, the recycle stream comprises any $C_6$ to $C_{12}$ aromatic or admixtures thereof. More preferably, the recycle stream comprises $C_6$ to $C_8$ aromatics, including benzene, toluene, xylene (the o-, m- and/or p-isomers of xylene), high aromatic reformate and/or BTX. By way of illustration, the weight ratio of aromatic recycle stream to paraffin feed is preferably in the range of 0.5:1 to 5:1. The conversion is undertaken while the recycle stream content of the cofeed passes through virtually unchanged.

In accordance with the invention, the feed and the recycle stream is introduced to a reactor containing a fixed or moving, e.g. possibly fluidized, catalyst bed of a catalyst described in detail below. The reactor preferably runs at elevated temperatures ranging from 400° C. to 700° C. and most preferably from 350° C. to 600° C. and most preferably at temperature ranging from 450°–600° C. The reactor inlet $H_2$/feed ratio is preferably zero (0). The weight hourly space velocity through the reactor is in the range of 0.1 to 50, preferably 0.5 to 10.

For recycle of the inert aromatic recycle stream, the product stream is resolved, e.g. by distillation, to provide a second aromatic recycle stream, and a product stream. A portion of the split stream is heated to about 300° to 650° C. in a separate heater either by direct firing or via indirect heat exchange with a superheated stream or other suitable heat exchange fluid and is then fed into admixture with fresh feed. Although it is preferred to recycle the aromatics stream, the aromatic recycle stream can be used in a once through operation.

Another aspect of the invention is the catalyst comprising a Group VIII or Group VIA metal and a non-acidic microporous material. The catalyst is non-acidic. As catalysts non-acidic forms of compositions used in the process exhibit extremely high selectivity for the paraffin conversion, under conditions described above The preferred catalysts are described in allowed U.S. patent application Ser. No. 418,377 filed Oct. 6, 1989, and its parent, U.S. Pat. No. 4,990,710, each of which is relied upon and incorporated by reference herein.

The amount of Group VIII or Group VIA metal in the catalyst can range from 0.01 to 30 weight percent and preferably 0.1 to 10 weight percent of the microporous material. In a preferred embodiment, platinum is the Group VIII metal. However, any Group VIII or Group VIA metal including those of the platinum group (platinum, iridium and palladium), chromium and vanadium can be employed.

In preferred catalysts, the microporous material contains tin as a modifier; the tin content of the microporous material can range from 0.01 to 20 weight percent. Practically, the tin content will range from 0.1 to 10 weight percent.

The preferred compositions comprising Group VIII (and/or Group VIA) metal combined with the microporous materials do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

The microporous materials of the catalysts are characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

Preferably, the microporous material has an X-ray diffraction pattern which corresponds to a zeolite, SAPO, ALPO, etc, and are thus crystalline as well as microporous. The preferred microporous materials are crystalline in the sense that they are identifiable as isostructural with zeolites by X-ray powder diffraction pattern.

In a preferred embodiment the pore size of the microporous crystalline tin containing silicates ranges from about 5 to about 8 Angstroms. In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein. The zeolite may alternatively be ZSM-11, ZSM-12, ZSM-22, ZSM-23, ZSM-35 and MCM-22. MCM-22 is described in U.S. Pat. No. 4,954,325 which is relied upon and incorporated by reference herein.

When, as in embodiments herein, the microporous material exhibits an X-ray diffraction pattern of a zeolite, at least some of the metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

The methods of synthesizing these preferred materials are described in U.S. Pat. No. 4,990,719 which is relied upon and incorporated by reference herein.

The non-acidic, microporous material, and Group VIII metal containing materials used in the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in the invention, the catalyst will preferably be combined with non-acidic matrix or binder materials. A preferred matrix or binder material would be silica or titania. The relative proportions of finely divided microporous material and inorganic oxide gel matrix vary widely, with the crystal content ranging from about 1 to about 90 percent by weight and more usually, particularly when the composite is prepared in the form of beads, in the range of about 2 to about 80 weight percent of the composite

EXAMPLES

Comparative Example

The catalyst employed was a 50% silica-bound Pt/Sn-ZSM-5 containing 0.63% Pt and 1.4% Sn.

The reaction was conducted at 550° C. by passing isobutane at 50 cc/min over 1 gram of catalyst A 38.6% yield of isobutene was observed.

EXAMPLE 1

In this Example the same catalyst and reaction conditions were used as in the Comparative Example. However, an equimolar amount of toluene (14.2 ml/hr) was cofed with the isobutane (50 cc/min.) reactant. The normalized yield of isobutene was increased to 47.2% at 550° C. At 500° C., a 32.7% yield of isobutene was obtained, with C3- products limited to 0.2 weight percent.

EXAMPLE 2

This Example illustrates the advantages of using aromatics diluent The equilibrium conversion of isobutane is 29% at 1 atm, 500° C. The conversion increases to 37.4% when the isobutane feed is diluted with an equal mole of aromatics such as benzene, toluene or xylenes. For an adiabatic fixed-bed reactor, the effect of aromatics dilution on reactor heat balance is shown as follows:

|  | iC4 | iC4:Benzene | iC4:Toluene | iC4:Xylenes |
| --- | --- | --- | --- | --- |
| Mole Ratio | 100 | 50:50 | 50:50 | 50:50 |
| iC4 Conversion, % | 29.0 | 37.4 | 37.4 | 37.4 |
| RxR Temp. Inlet, °C. | 669 | 613 | 602 | 594 |
| RxR Temp. Outlet, °C. | 500 | 500 | 500 | 500 |
| Delta Temperature | 169 | 113 | 102 | 94 |

The calculated heat balance suggests that the aromatics dilution enhances the conversion (37.4 vs. 29.0%) and lowers significantly the inlet temperature at a required outlet temperature of 500° C. Aromatics with higher MW are more effective in reducing the delta temperature due to their higher heat capacity With a BTX stream (48:28:24 mole ratio of B:T:X) readily available in the refinery, the 50:50 dilution with isobutane feed requires the inlet temperature of 605° C. Similar to a reforming operation, paraffin dehydrogenation reaction is endothermic, thus the temperature at the reactor outlet will be significantly lower than that of the inlet. The aromatics diluent serves as a heat carrier to balance the heat loss due to endothermic reactions, thus maintaining the lower temperature drop across the reactor.

Increasing the dilution ratio will enhance the conversion as well as heat balance. Decreasing the partial pressure of light paraffin feed in the reactor, can enhance equilibrium dehydrogenation conversion The upper limit of dilution ratio is determined by the activity of the catalyst (kinetic effect) The dilution ratio ranges from 10% to 70% at the reactor inlet with or without recycle stream.

Thus it is apparent that there has been provided, in accordance with the invention, a process, that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A process for catalytically converting a $C_2$-$C_5$ alkane to a $C_2$-$C_5$ alkene, comprising
    heating an aromatic recycle stream, and passing the heated aromatic recycle stream to a catalyst bed in which the catalyst is non-acidic and comprises a Group VIA or Group VIII metal and a non-acidic microporous material
        wherein the amount of Group VI or Group VIII metal in the catalyst can range from 0.1 to 30 weight percent
    contacting a $C_2$-$C_5$ alkane containing feed with the catalyst bed in a reactor maintained at a catalytic conversion temperature ranging from 350° to 600° C., in the presence of said aromatic recycle stream to produce a product effluent;
    stripping, from the product effluent resulting from said contacting, at least a portion of said aromatic recycle stream; and
    wherein the product effluent contains an amount of $C_2$-$C_5$ alkene which exceeds the amount of $C_2$-$C_5$ alkene in the feed.

2. The process of claim 1, wherein the process is undertaken in the absence of purposefully added hydrogen.

3. The process of claim 1, wherein the aromatic recycle stream is heated to within about 50° C. of the catalytic conversion temperature.

4. The process of claim 1, wherein the aromatic recycle stream has an initial boiling point which is at least 40° C. above the boiling point of a $C_2$-$C_5$ alkane containing feed.

5. The process of claim 1, wherein the material exhibits the X-ray diffraction pattern of a zeolite.

6. The process of claim 5 wherein the zeolite is selected from the group consisting of ZSM-5, ZSM-11, ZSM-12, ZSM-22, ZSM-23, ZSM-35, and MCM-22.

7. The process of claim 6, wherein the zeolite is ZSM-5.

8. The process of claim 1, wherein the metal is platinum and the non-acidic microporous material contains tin in an amount of 0.01 to 20 weight percent of the non-acidic microporous material.

9. The process of claim 7, wherein the metal is platinum and the non-acidic microporous material contains tin in an amount of 0.01 to 20 weight percent of the non-acidic microporous material.

10. The process of claim 1, which further includes catalytic conversion conditions of a weight hourly space velocity of 0.1 to 50.

11. The process of claim 1, wherein the combined aromatic recycle stream and the alkane containing feed provide a charge with a weight ratio of aromatic recycle stream to alkane containing feed in a range of 0.5:1 to 5:1.

12. The process of claim 1, which includes heating the aromatic recycle stream to 300° to 650° C.

13. The process of claim 1, wherein the aromatic recycle stream comprises any $C_6$ to $C_{12}$ aromatic or admixtures thereof.

14. The process of claim 13, wherein the recycle stream comprises $C_6$ to $C_8$ aromatics.

15. A process for catalytically converting isobutane to isobutene, comprising
    heating an aromatic recycle stream and passing the heated aromatic recycle stream to a catalyst bed in which the catalyst comprises a Group VIA or Group VIII metal and a non-acidic microporous material
        wherein the amount of Group VIA or Group VIII metal in the catalyst can range from 0.1 to 30 weight percent
        wherein the non-acidic microporous material exhibits the X-ray diffraction pattern of a zeolite, wherein the zeolite is selected from the group consisting of ZSM-5, ZSM-11, ZSM-12 ZSM-22, ZSM-23, ZSM-35 and MCM-22;
    contacting the isobutane containing feed with the catalyst bed in a reactor maintained at a catalytic conversion temperature ranging from 350° to 600° wherein heat for said catalytic conversion temperature is provided by said heated recycle stream, to produce isobutene;
    separating from a product effluent resulting from said contacting said aromatic recycle stream.

16. The process of claim 15, wherein the metal is platinum and the microporus material contains 0.01 to 20 weight percent of tin.

17. The process of claim 16, wherein the zeolite is ZSM-5.

18. The process of claim 15, which further includes catalytic conversion conditions of a weight hourly space velocity of 0.1 to 50.

19. The process of claim 18, wherein the process is undertaken in the absence of purposefully added hydrogen.

20. The process of claim 15, which includes heating the aromatic recycle stream to 300° to 650° C.

21. The process of claim 20, wherein the aromatic recycle stream comprises any $C_6$ to $C_{12}$ aromatic or admixtures thereof 22. The process of claim 21, wherein the recycle stream comprises $C_6$ to $C_8$ aromatics.

23. The process of claim 15, wherein the combined aromatic recycle stream and the isobutane containing feed provide a charge with a weight ratio of aromatic recycle stream to isobutane containing feed in a range of 0.5:1 to 5:1.

24. A process for catalytically converting isopentane to isopentene, comprising heating an aromatic recycle stream and passing the heated aromatic recycle stream to a catalyst bed in which the catalyst comprises a Group VIA or Group VIII metal and a non-acidic microporous material wherein the amount of Group VIA or Group VIII metal in the catalyst can range from 0.1 to 30 weight percent wherein the non-acidic microporous material exhibits the X-ray diffraction pattern of a zeolite, wherein the zeolite is selected from the group consisting of ZSM-5, ZSM-11, ZSM-12, ZSM-22, ZSM-23, ZSM-35 and MCM-22;

contacting the isopentane containing feed with the catalyst bed in a reactor maintained at a catalytic conversion temperature ranging from 350° to 600° C. wherein heat for said catalytic conversion temperature is provided by said heated recycle stream, to produce isopentene;

separating, from a product effluent resulting from said contacting, said aromatic recycle stream.

25. The process of claim 24, wherein the metal is platinum and the microporous material contains 0.01 to 20 weight percent of tin.

26. The process of claim 25, wherein the zeolite is ZSM-5.

27. The process of claim 24, which further includes catalytic conversion conditions of a weight hourly space velocity of 0.1 to 50.

28. The process of claim 24, wherein the combined aromatic recycle stream and the isobutane containing feed provide a charge with a weight ratio of aromatic recycle stream to isobutane containing feed in a range of 0.5:1 to 5:1.

29. The process of claim 24, which includes heating the aromatic recycle stream to 300° to 650° C.

30. The process of claim 24, wherein the aromatic recycle stream comprises any $C_6$ to $C_{12}$ aromatic or admixtures thereof.

31. The process of claim 30, wherein the recycle stream comprises $C_6$ to $C_8$ aromatics.

32. The process of claim 24, wherein the combined aromatic recycle stream and the isopentane containing feed provide a charge with a weight ratio of aromatic recycle stream to isopentane containing feed in a range of 0.5:1 to 5:1.

* * * * *